(12) United States Patent
Henry et al.

(10) Patent No.: US 9,732,043 B2
(45) Date of Patent: Aug. 15, 2017

(54) PROCESS FOR PREPARING 5-AMINO-2,3-DIHYDROPHTHALAZINE-1,4-DIONE MONOSODIUM SALT

(71) Applicant: BACH PHARMA, INC, North Andover, MA (US)

(72) Inventors: Mark O. Henry, North Andover, MA (US); William S. Lynn, Hillsborough, NC (US)

(73) Assignee: Bach Pharma, Inc., North Andover, MA (US)

( * ) Notice: Subject to any disclaimer, the term of this patent is extended or adjusted under 35 U.S.C. 154(b) by 0 days.

(21) Appl. No.: 14/615,704

(22) Filed: Feb. 6, 2015

(65) Prior Publication Data
US 2016/0237039 A1   Aug. 18, 2016

Related U.S. Application Data

(63) Continuation of application No. 12/701,088, filed on Feb. 5, 2010, now abandoned.

(60) Provisional application No. 61/150,581, filed on Feb. 6, 2009.

(51) Int. Cl.
*C07D 237/32* (2006.01)
(52) U.S. Cl.
CPC ........... *C07D 237/32* (2013.01); *Y10T 436/17* (2015.01)

(58) Field of Classification Search
CPC .................................................... C07D 237/32
USPC .......................................................... 544/237
See application file for complete search history.

(56) References Cited

U.S. PATENT DOCUMENTS 6,489,326 B1 * 12/2002 Abidov ................ C07D 237/32
514/248

OTHER PUBLICATIONS

Drew, et al. Journal of the Chemical Society, 1937, 26-33.*

* cited by examiner

*Primary Examiner* — Douglas M Willis
(74) *Attorney, Agent, or Firm* — Occhiuti & Rohlicek LLP

(57) ABSTRACT

The present invention comprises methods of manufacturing a highly purified, pharmaceutical grade phthalazinedione (for example, 5-amino-2,3-dihydrophthalazine-1,4-dione) for administration to a human or animal. The manufacturing methods identify and isolate starting materials (for example, 3-nitrophthalic acid), and prepare intermediate products (for example, 3-nitrophthalhydrazide), which are suitable for the commercial batch process production of highly purified and high-yielding intermediate products and final phthalazinedione products. In an embodiment, a solution of 3-nitrophthalhydrazide and sodium hydroxide in water is prepared and hydrogenated to yield 5-amino-2,3-dihydrophthalazine-1,4-dione.

15 Claims, No Drawings

PROCESS FOR PREPARING 5-AMINO-2,3-DIHYDROPHTHALAZINE-1,4-DIONE MONOSODIUM SALT

This application is a continuation of U.S. application Ser. No. 12/701,088 filed on Feb. 5, 2010, which is entitled to the benefit of earlier filed U.S. Provisional Patent Application No. 61/150,581, filed on Feb. 6, 2009 under 35 U.S.C. §119(e), the entire disclosures of which are hereby incorporated by reference herein.

CROSS-REFERENCE TO RELATED APPLICATIONS

This application is entitled to the benefit of earlier filed U.S. Provisional Patent Application Ser. No. 61/150,581 filed on Feb. 6, 2009 under 35 U.S.C. §119(e), the entire disclosure of which is hereby incorporated by reference herein.

BACKGROUND

In healthy cells, a balance of redox reactions maintains a physiologically appropriate environment for various cellular functions related to growth, differentiation, activity, and death. The proper coordination of such functions ensures homeostasis and the health of cells. Research has shown that alterations in cellular redox status affect activities such as cellular signaling, suggesting that altering the cellular redox status could also affect cellular activation, which results from certain cellular signals (U.S. Pat. No. 5,994,402). Altering the intracellular redox state by depleting cells of glutathione (GSH), an endogenous "redox agent," has also been shown to protect cells from certain injury and to promote their survival (U.S. Pat. No. 5,994,402), again suggesting a link between alterations in the cellular redox state and cellular functions.

An imbalanced redox state, even if not the cause of a particular disease condition, may facilitate that condition by providing an "unhealthy" environment in which necessary cellular functions become impaired. Cellular redox status may become impaired in numerous disease conditions. Under the stress of a disease state, the rate of redox reactions increases or decreases as needed by the cell. Significant or prolonged deviations in the intracellular redox status disable cellular processes, including defense mechanisms. When such cellular functions are impaired, the survival of the cell becomes uncertain. Maintenance of the proper redox status is thus critical to the fate of the cell.

To counter and correct disturbances in the redox status, cells require agents that can modulate redox imbalances, to facilitate reduction or oxidation reactions as appropriate. Agents currently available for correcting redox imbalances are inadequate in that they are labile, quickly oxidized, or unable to translocate to the proper region of the cell. Examples of such exogenous redox agents include cysteine, reduced lipoates or thiols, glucocorticoids, and other antioxidants. Redox agents that remain stable, active, and functional in the cellular environment are necessary.

Phthalazinediones and phthalazinedione derivatives have been described as effective against certain conditions associated with redox imbalances such as inflammation, cancer, arrhythmia, hyperlipidemia, and hypoxia (U.S. Pat. Nos. 6,686,347; 6,489,326; 5,874,444; 5,543,410; 5,512,573; 4,861,778; 4,250,180; Hall et al., Biomed. Biochim. Acta. A1: 423-433 (1988); Hall et al., J Pharm. Pharmacol. 41: 394-397 (1989); Hall et al., Anticancer Drugs. 3: 55-62 (1992); Burner et al., Int. J. Tissue React. 18: 47-55 (1996)). However, toxicity and the lack of pharmacological activity of certain phthalazinediones, including 2,3-dihydrophthalazine-1,4-dione and 5-amino-2,3-dihydrophthalazine-1,4-dione, were also noted (U.S. Pat. Nos. 6,489,326; 5,543,410; 5,512,573).

SUMMARY

The present invention has been made in consideration of the above problems. The present invention relates to a method for manufacturing a highly purified phthalazinedione. More particularly, the present invention is directed to methods of manufacturing a highly purified phthalazinedione product suitable for use as a pharmaceutical in the treatment of humans or other animals. More specifically, the present invention relates to methods of manufacturing a pharmaceutical grade phthalazinedione in compliance with GMP standards.

Certain embodiments of the invention include a process for the reproducible preparation of a highly purified pharmaceutical grade phthalazinedione comprising a first step of identifying and isolating a starting material having a purity that is suitable for preparing a highly purified final phthalazinedione product that is of pharmaceutical grade. The process also comprises at least one additional step wherein the identified and isolated starting material is chemically treated to form a pharmaceutical grade final phthalazinedione product. The final phthalazinedione product, in certain embodiments, has a purity of at least 90% and is made with a process that complies with GMP reproducibility standards.

In certain other embodiments of the invention, a process for preparing a highly purified pharmaceutical grade phthalazinedione is disclosed. The process comprises a first step of identifying and isolating a highly purified starting material that is suitable for the preparation of a highly purified pharmaceutical grade final phthalazinedione product. The identified and isolated highly purified starting material is chemically treated to form a highly purified intermediate product suitable for the preparation of the pharmaceutical grade final phthalazinedione product. The highly purified intermediate product is chemically treated to form the pharmaceutical grade final phthalazinedione product. In certain further embodiments, the starting material is at least 90% pure as determined by HPLC. In certain other embodiments, the starting material is a highly purified form of 3-nitrophthalic acid. In certain other embodiments, the intermediate product is at least 90% pure as determined by HPLC. In certain other embodiments, the intermediate material is a highly purified form of 3-nitrophthalhydrazide.

In certain other embodiments of the process for reproducible preparation of the highly purified pharmaceutical grade phthalazinedione, the final phthalazinedione product meets the standard GMP requirements. In certain other embodiments the final phthalazinedione product is capable of crossing the human blood-brain barrier. In certain further embodiments, the final phthalazinedione product has a molecular weight of less than 500 grams-mol$^{-1}$. In other embodiments, the final phthalazinedione product has a molecular weight of 199.14 grams-mol$^{-1}$.

In certain other embodiments of the process for reproducible preparation of the highly purified pharmaceutical grade phthalazinedione, the process is a commercial batch process.

In certain other embodiments of the process for reproducible preparation of the highly purified pharmaceutical grade phthalazinedione, the intermediate product has a product yield of at least 20 wt %. In more preferable embodiments, the intermediate product has a product yield of at least 30 wt %. In certain other embodiments, the intermediate product has a product yield of at least 40 wt %.

In certain other embodiments of the process for reproducible preparation of the highly purified pharmaceutical grade phthalazinedione, the highly purified form of 3-nitrophthalic acid starting material is at least 95% pure as determined by HPLC analysis. In certain other embodiments the 3-nitrophthalic acid starting material is at least 99.9% pure as determined by HPLC analysis. In other more preferred embodiments, the 3-nitrophthalhydrazide intermediate product is at least 95% pure as determined by HPLC analysis. In certain other embodiments, the 3-nitrophthalhydrazide intermediate product is at least 99.9% pure as determined by HPLC analysis. In certain embodiments, the final phthalazinedione has a purity of at least 95% as determined by HPLC analysis. In certain other specific embodiments, the final phthalazinedione product has a purity of at least 99.6% as determined by HPLC analysis.

In certain other specific embodiments of the process for reproducible preparation of the highly purified pharmaceutical grade phthalazinedione, the identified and isolated highly purified starting material is 3-nitrophthalic acid having a purity of at least 99% as determined by HPLC analysis. The highly purified intermediate product is 3-nitrophthalhydrazide having a purity of at least 99% as determined by HPLC analysis, and wherein the pharmaceutical grade final phthalazinedione product is monosodium luminol having a product yield of at least 20 wt % and a purity of at least 99.6% as determined by HPLC analysis.

In certain further embodiments, the starting material is identified by performing an HPLC analysis of a composition that includes the starting material to identify a starting material suitable for preparation of a pharmaceutical grade phthalazinedione and then isolating the highly purified starting material under conditions such that the starting material is at least 90% pure.

In certain other embodiments of the process for reproducible preparation of the highly purified pharmaceutical grade phthalazinedione, the process includes a process for identifying a highly purified starting material suitable for use in preparing a highly purified pharmaceutical grade phthalazinedione product. This process includes performing an HPLC analysis of a composition including the starting material to so as to identify a starting material suitable for preparation of a pharmaceutical grade phthalazinedione product and subsequently isolating the highly purified starting material under conditions such that the identified and isolated starting material is at least 90% pure. In certain other embodiments, the starting material is more preferably at least 95% pure. In other embodiments, the starting material is at least 99% pure. In certain other embodiments the starting material is a highly purified form of 3-nitrophthalic acid. In certain other embodiments, the 3-nitrophthalic acid has a purity of at least 95% as determined by HPLC analysis.

In certain other embodiments of the present invention, a process for reproducibly preparing a highly purified intermediate product suitable for use in preparing a highly purified pharmaceutical grade final phthalazinedione product is disclosed. The process comprising the steps of identifying and isolating a highly purified starting material suitable for use in preparing a pharmaceutical grade final phthalazinedione product and chemically treating the identified and isolated highly purified starting material to form a highly purified intermediate product suitable for the preparation of the highly purified pharmaceutical grade final phthalazinedione product.

In certain embodiments of the process of reproducibly preparing the highly purified intermediate product, the highly purified intermediate product is at least 99% pure as determined by HPLC analysis. In certain other embodiments, the highly purified intermediate product is at least 99% pure as determined by HPLC analysis. In certain other embodiments, the intermediate product has a product yield of at least 20 wt %. In certain more preferred embodiments the intermediate product has a product yield of at least 30 wt %. In certain other preferred embodiments, the intermediate product has a product yield of at least 40 wt %. In certain other embodiments, the highly purified intermediate product is at least 99% pure as determined by HPLC analysis.

Certain other embodiments of the present invention provide a pharmaceutical composition including the highly purified pharmaceutical grade final phthalazinedione product. In certain embodiments, the composition is prepared according to any of the embodiments disclosed above. In certain embodiments, the final phthalazinedione product is at least 99% pure. In certain other embodiments, the final phthalazinedione product is at least 99.6% pure as determined by HPLC analysis. In certain further embodiments, the final phthalazinedione product is monosodium luminol.

In certain specific embodiments of the invention, a final phthalazinedione product is disclosed having a purity of at least 95% or more preferably 99%. In certain other specific embodiments, a final phthalazinedione product is disclosed having a purity of at least 99.6%. In further embodiments of the present invention, the final phthalazinedione product is a monosodium luminol having a purity of at least 99%. In certain other embodiments of the present invention, a pharmaceutical grade product is provided that is monosodium luminol having a purity of at least 99.6%.

In other embodiments, the invention provides a cosmetic composition comprising the final phthalazinedione product as described in any of the embodiments above. In yet further embodiments, the cosmetic composition is in a cosmetically acceptable form selected from the group consisting of tablet, capsule, granule, powder, solution, suspension, microsphere, liposome, colloid, lyophilized composition, gel, lotion, ointment, cream, spray, and suppository. In other embodiments, the cosmetic composition comprises a second compound selected from the group consisting of an amino acid, antibiotic, antiviral agent, anti-inflammatory agent, antioxidant, immunomodulator, reductant, oxidative protector, steroid, and vitamin. In further specific embodiments of this invention, the second compound is glutathione, glucocorticoid, dexamethasone, cysteine, lipoic acid, biopterin, hydralazine, rasagiline, thiorecdoxin, ferulic acid, minocycline, menadione, tetracycline, isosorbate dinitrate, dextromethorphan, dithiothreitol, carnosine, or clomethiazole.

DETAILED DESCRIPTION

The term "pharmaceutical grade," as used herein, means that certain specified biologically active and/or inactive components in the drug must be within certain specified absolute and/or relative concentration, purity and/or toxicity limits and/or that the components must exhibit certain activity levels as measured by a given bioactivity assay. Pharmaceutical grade further incorporates suitability for administration by means including topical, ocular, parenteral, nasal, mucosal, vaginal, anal, and the like.

A "pharmaceutical" as used herein, refers to any substance intended for use in the diagnosis, cure, mitigation, treatment, or prevention of disease, injury, illness or irregularity and also includes cosmetic and neutraceutical use.

The term "yield" or "product yield" as used herein, refers to the weight of the final phthalazinedione product, or the weight of the intermediate product, in terms of a weight percent (wt %) of the starting material.

The term "purity," as used herein, means the percent weight of the in-hand, isolated sample of starting material, intermediate, or final phthalazinedione product relative to the starting material, intermediate, final phthalazinedione product respectively, plus any impurities, additives, excipients, or the like, at the relevant stage. The purity may be determined by any conventional method known to those in the art, such as HPLC assay or mass spectroscopy.

The term "reproducibility," or "reproducible," as used herein, refers to the reproducibility requirements under the Good Manufacturing Practices standards of the United States. The term as used herein, further refers to the ability to consistently produce the same results from batch to batch contemporaneously or at different time periods, using the same batch or different batches.

The term "final phthalazinedione product," as used herein, refers to the phthalazinedione end-product resulting from the chemical treatment of the intermediate product. It is the final product prepared from the chemical treatment of the starting material and/or the intermediate material.

The term "intermediate product," as used herein, refers to the result of the chemical treatment of the starting material. The intermediate product is chemically treated as described herein below to obtain a highly purified phthalazinedione product as described herein below.

The term "intermediate," "intermediate material" or "intermediate product," as used herein, refers to whatever components are present following the identification and chemical treatment of suitable starting material and prior to formation of the final phthalazinedione product.

The term "starting material" or "starting product," as used herein, refers to any mixture or composition, pure or impure, containing a material that is suitable for the preparation of a highly purified final phthalazinedione product. It is also further understood that highly purified starting material used herein is identified by HPLC or any other suitable method of identifying the purity of a chemical substance.

The term "chemically treating," as used herein, refers to the process by which the starting material, or intermediate product, is placed in a chemical reaction process. In the chemical reaction process the starting material is chemical reacted with other chemicals suitable for producing an intermediate product that is suitable for producing a highly purified final phthalazinedione product as defined herein. The chemical reaction process may also include the intermediate product and other chemicals, such that their interaction with the intermediate product in the chemical reaction process is suitable for producing a highly purified final phthalazinedione product as defined herein.

The term "suitable for preparation" or "suitable starting material," as used herein, refers to the purified forms of starting or intermediate materials that can be chemically treated and converted into a final phthalazinedione that is highly purified.

The term "suspension," as used herein, refers to a finely divided, undissolved active ingredient suspended in a solvent.

The term "GMP," as used herein, refers to the Good Manufacturing Practices standards of the United States.

The term "HPLC," as used herein, refers to High Pressure Liquid Chromatography. HPLC is a form of column chromatography used in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

The term "IPC," as used herein, refers to Iron Pairing Chromatography.

Identifying and Isolating the Starting Material:

In certain embodiments of the present invention, a starting material is chosen that is suitable for use in preparing a highly purified final phthalazinedione. In certain embodiments, the starting material is identified for its suitability in being chemically treated as described herein to prepare a final phthalazinedione product which has a purity of at least 90%. The starting material is selected based on its purity. Starting materials that are less than 90% pure are discarded.

In identifying and isolating the suitable starting material, a composition having the starting material is analyzed. In this process an analysis of the purity of the composition including the staring material is performed so as to obtain an identified starting material that is suitable for preparing the final phthalazinedione product. The identified starting material is isolated so as to produce an identified and isolated starting material. The identified and isolated starting material is at least 90% pure. In certain embodiments, the purity of the starting material is determined by HPLC analysis. However, any other tool of chemical analysis known to those of skill in the art may be used to determine the purity such as mass spectroscopy.

In certain embodiments of the present invention, the starting material is a 3-nitrophthalic acid. In certain other specific embodiments, the 3-nitrophthalic acid is highly purified. In certain embodiments, the staring material is at least about 90% pure. In certain other embodiments, the starting material is at least 95% pure, or more preferably at least about 99% pure or more preferably at least 99.9% pure. The purity of the starting material also includes 91%, 92%, 93%, 94%, 96%, 97%, 98%, 99.1%, 99.2%, 99.3%, 99.4%, 99.5%, 99.6%, 99.7%, 99.8% and all specific values, ranges and subranges therewithin. In certain embodiments of this invention, in using the starting material to produce a final phthalazinedione product that is highly purified, an intermediate product is first produced from the starting material. In certain embodiments, this intermediate product must also have a purity of at least 90% so as to produce a highly purified final phthalazinedione product that is suitable for pharmaceutical use. In certain embodiments this intermediate product has a product yield of at least 20 wt % of the starting material or more preferably at least 30 wt % or most preferably at least 40 wt %. In other embodiments, the final phthalazinedione product has a yield of at least 20 wt % of the starting material or more preferably at least 30 wt % or most preferably at least 40 wt %. For example, a starting batch of 2000 lbs of the identified and isolated highly purified starting material yields between 400 lb and 800 lbs of suitable intermediate product.

While not wishing to be bound by any specific theory, it is believe that the product yield of the highly purified final phthalazinedione is limited by the purity of the starting material and any generated intermediate product. Moreover, the purity of the intermediate is partly limited by the purity of the starting material and the purity of the final phthalazinedione product is partly limited by the purity of the starting material and the intermediate product. In certain embodiments of the present invention, a purified form of 3-nitrophthalic acid is identified and isolated for use in preparing a pharmaceutical grade highly purified form of a final phthalazinedione product. The highly purified starting material is identified from any mixture containing the starting material and is isolated such that the starting material has a purity suitable for producing a highly purified final phthalazinedione product. The starting material in certain embodiments is at least 90% pure. In certain other embodiments, the identified and isolated starting material is at least 95% pure. In certain other embodiments, the purity of the starting material is at least 99%. In more preferred embodiments, the identified and isolated starting material is at least 99.9% pure. In certain embodiments, the final phthalazinedione is luminol (5-amino-2,3-dihydro-1,4-phthalazinedione) or more preferably sodium luminol or any other derivative, analog or salt thereof.

Converting the Starting Material to an Intermediate:

In certain embodiments of the present invention, a process is disclosed for reproducibly preparing a highly purified intermediate product suitable for use in preparing a highly purified pharmaceutical grade final phthalazinedione product. In preparing an intermediate suitable for use in preparing a highly purified, pharmaceutical-grade, final phthalazinedione product, a starting material that is highly purified is identified and isolated according to the process described above for identifying and isolating a suitable starting material. The identified and isolated highly purified starting material is chemically treated to form a highly purified intermediate product suitable for use in preparing a highly purified pharmaceutical grade final phthalazinedione product.

In certain embodiments, the highly purified final phthalazinedione product is of pharmaceutical grade and high purity. To meet the standards of pharmaceutical grade, the final phthalazinedione product is prepared such that it is suitable for human or animal ingestion without significant toxicity. In certain more specific embodiments, the final phthalazinedione product is produced such that both the product and process complies with GMP requirements. In certain embodiments, the purity of the final phthalazinedione product is at least 90% or more preferably at least 95% or more preferably at least 99%, or most preferably at least 99.6%. In certain embodiments, the starting material is identified and isolated such that its purity is at least 90%. The purity of the starting material, intermediate and final phthalazinedione also includes 91%, 92%, 93%, 94%, 96%, 97%, 98%, 99.1%, 99.2%, 99.3%, 99.4%, 99.5%, 99.6%, 99.7%, 99.8% and all specific values, ranges and sub-ranges therewithin. In certain other embodiments, the starting material is chemically treated and converted to an intermediate product that is itself suitable for use in the preparation of the final phthalazinedione. In certain embodiments, the intermediate product is prepared such that the purity is at least 90%. The final phthalazinedione product is then prepared from the highly purified form of the intermediate such that the final phthalazinedione product is of pharmaceutical grade and is highly purified.

In certain embodiments of the present invention, the intermediate product is highly purified. The intermediate is prepared and isolated such that it is suitable for use in preparing a highly purified final phthalazinedione product. The purity of the intermediate is at least 90%, or preferably at least 95%, more preferably at least 99% and most preferably at least 99.6%. The purity of the intermediate also includes 91%, 92%, 93%, 94%, 96%, 97%, 98%, 99.1%, 99.2%, 99.3%, 99.4%, 99.5%, 99.6%, 99.7%, 99.8% and all specific values, ranges and sub-ranges therewithin. In certain embodiments, the purity of the intermediate product is determined by HPLC analysis. In certain embodiments, the purity is determined by any other method of analysis known to those skilled in the art.

In certain embodiments of the process of reproducibly preparing a purified form of the intermediate product, the starting material is at least 90% pure. In certain preferred embodiments, the starting material is at least 95% pure. In certain more preferred embodiments, the starting material is at least about 99% pure. In the most preferred embodiments, the starting material is at least about 99.9% pure. The purity of the starting material is determined by HPLC or any other method of identifying the purity of the starting material known to those skilled in the art, such as mass spectroscopy. In other embodiments of this invention, the starting material is a highly purified form of 3-nitrophthalic acid.

In certain further embodiments of the present invention, the intermediate product is 3-nitrophthalhydrazide. The 3-nitrophthalhydrazide is prepared by hydrating the identified and isolated highly pure starting material. The hydrating agent in certain embodiments includes hydrazine hydrate. In certain specific embodiments, the 3-nitrophthalhydrazide is a highly purified form having a purity of at least 90%, more preferably at least 95%, more preferably at least 99%, and yet more preferably at least 99.9%.

In certain embodiments, the intermediate product has a product yield that is suitable for commercial processing. Suitable yield for commercial processing affords the production of an intermediate product that is at least 20 wt % of the starting material's weight. In certain embodiments of the present invention, the yield of the intermediate is at least 20 wt % of the starting material. In certain other embodiments the yield of the intermediate is at least 30 wt % and most preferably at least 40 wt % of the starting material. The yield of the intermediate also includes yields ranging from 20% to 30% and from 30% to 40% and all specific values and sub-ranges therewithin. The weight percentage of the yield herein discussed is determined by comparing the weight of the intermediate product to the weight of the starting material.

In preparing the highly purified intermediate, a suitable starting material, as described above, is identified and isolated. In some embodiments, the starting material is a highly purified form of 3-nitrophthalic acid. In certain further embodiments, the highly purified starting material is suspended in a solution of a weak acid and water. In some embodiments, a suspension is formed. In certain other embodiments, the weak acid includes acetic acid. The suspension is then warmed and hydrated. In certain specific, though not exhaustive of the possible embodiments, the suspension is charged with hydrazine hydrate over 1 to 2 hours. The hydrazine hydrate used for charging the suspension may be in aqueous form. In further embodiments, the suspension is optionally charged with additional hydrazine hydrate and warmed back to reflux and subsequently heated for a further 4 to 10 hours or more preferably 6 to 8 hours. In certain specific, though not exhaustive embodiments, the suspension is warmed to a temperature of about 50° C. to about 80° C. In yet further embodiments, the suspension is warmed to about 60° C. to about 75° C. In subsequent steps, the hydrated solution is then cooled to about 40° C. to about 70° C. or more preferably about 50° C. to about 60° C. and sampled for IPC. The solution is then further cooled to about 10° C. to about 30° C. or more preferably to about 14° C. to about 20° C. The intermediate product is then isolated. In other possible embodiments, the intermediate product is isolated by filtration. The isolated intermediate product is then washed and dried to constant weight. In further embodiments the isolated intermediate product is washed twice with water (2 vol. each) and dried under vacuum at about 40° C. to about 70° C. or more preferably to about 50° C. to about 60° C.

In certain embodiments of the present invention, the purity of the starting material is identified such that a commercial batch process for the production of the final phthalazinedione is practical and possible. A commercial batch process is practicable where a batch or continuous batch of the starting material yields the purified final phthalazinedione in an amount at least 20 wt %, or more preferably at least 30 wt % or most preferably at least 40 wt %, of the starting material. To produce a highly purified final phthalazinedione product, the starting material is identified by HPLC analysis to confirm it's purity. The purity of the starting material is at least 90%. More preferably, the purity of the starting material is at least 95%. In certain other preferred embodiments the identified starting material is at least 99% pure while in other embodiments the identified starting material is at least 99.9% pure. In certain embodiments, the highly purified final phthalazinedione is at least 90% pure, or more preferably at least 95% pure. In still yet more preferred embodiments the final phthalazinedione product is at least 96.4% pure, while in other embodiments the final phthalazinedione product is at least 99% or 99.9% pure. The purity of the final phthalazinedione product also includes 91%, 92%, 93%, 94%, 96%, 97%, 98%, 99.1%, 99.2%, 99.3%, 99.4%, 99.5%, 99.6%, 99.7%, 99.8% and all specific values, ranges and sub-ranges therewithin.

In certain exemplary description of the batch processes used to produce the intermediate product, a batch containment having the capacity for 2000 pounds (lbs) is filled with the starting material and a weak acid such that a suspension is formed. The starting material has a weight of about 2000 lbs. Through chemical treatment as described above, the starting material is hydrated, for example, with hydrazine hydrate. A reaction product containing the purified form of the intermediate is produced from the reaction of the starting material with the hydrazine hydrate. The intermediate product is isolated from the intermediate product such that 400 lbto about 800 lbs of the intermediate product, having a purity of at least 90% is secured for use in producing the final phthalazinedione product. In certain embodiments, the starting material is 3-nitrophthalic acid and the intermediate product is 3-nitrophthalhydrazide. The production of the intermediate product satisfies the consistency requirements of United States GMP. The GMP standards of other states, including Canada, Europe, China, Australia and Japan, for example, are also contemplated.

In certain specific embodiments of the present invention, the intermediate product is a highly purified form of 3-nitrophthalhydrazide that has a purity of at least 90%, preferably at least 95%, more preferably at least 99% and most preferably at least 99.9% and having a product yield of at least 20 wt %, preferably at least 30 wt %, more preferably at least 40 wt %. The 3-nitrophthalhydrazide is suitable for use in preparing a pharmaceutical grade phthalazinedione such as sodium luminol or a salt thereof, wherein the sodium luminol or salt thereof is at least 90% pure as determined by HPLC or more preferably, more preferably at least 95% pure and most preferably at least 99.6% pure. The sodium luminol has a product yield of at least 20 wt % or more preferably at least about 30 wt % and most preferably at least 40 wt %.

In certain embodiments of the invention, a commercial batch process is employed for the production of the final pharmaceutical-grade, highly purified phthalazinedione, such as sodium luminol. A batch of 1600 lbs of a highly purified form of 3-nitrophthalic acid is loaded into a reactor and the highly purified starting material is suspended in a solution of a weak acid and water. In some embodiments, a suspension is formed. In certain specific, though not exhaustive of the possible embodiments, the weak acid includes acetic acid. The suspension is then warmed and hydrated. In some embodiments, the suspension is charged with hydrazine hydrate over 1 to 2 hours. In certain embodiments, the suspension is optionally charged with additional hydrazine hydrate and warmed back to reflux and subsequently heated for a further 4 to 10 hours or more preferably 6 to 8 hours. In certain other embodiments, the suspension is warmed to a temperature of about 50° C. to about 80° C. In further embodiments, the suspension is warmed to about 60° C. to about 75° C. In subsequent steps, the hydrated solution is then cooled to about 40° C. to about 70° C. or more preferably about 50° C. to about 60° C. and sampled for IPC. The solution is then further cooled to about 10° C. to about 30° C. or more preferably to about 14° C. to about 20° C. At least 200 lbs, and more preferably at least 400 lbs, of the isolated intermediate product is then isolated. In other embodiments, the intermediate product is isolated by filtration. The isolated intermediate product is then washed and dried to constant weight. In yet further embodiments, the isolated intermediate product is washed twice with water (2 vol. each) and dried under vacuum at about 40° C. to about 70° C. or more preferably to about 50° C. to about 60° C.

Preparation of Pharmaceutical-Grade Phthalazinedione:

In certain embodiments of the invention, a final phthalazinedione product of pharmaceutical grade is prepared from an intermediate product, as described above, such that the final phthalazinedione product is highly purified. In certain embodiments, the highly purified final phthalazinedione product has a surprisingly high purity and product yield. In certain embodiments, the purity of the final phthalazinedione is at least 90%, more preferably at least 95% and even more preferably at least 99%. In certain further embodiments, the purity of the final phthalazinedione is at least 99.6%. The purity of the final phthalazinedione product also includes 91%, 92%, 93%, 94%, 96%, 97%, 98%, 99.1%, 99.2%, 99.3%, 99.4%, 99.5%, 99.6%, 99.7%, 99.8% and all specific values, ranges and sub-ranges therewithin. In certain embodiments, the final phthalazinedione product has a product yield of at least 20 wt %, more preferably at least 30 wt % and most preferably at least 40 wt %. The yield of the final phthalazinedione product also includes yields ranging from 20% to 30% and from 30% to 40% and all specific values and sub-ranges therewithin.

In certain embodiments of the present invention a process for reproducibly producing a highly purified pharmaceutical grade final phthalazinedione product from a highly purified identified and isolated starting material is provided. The process comprising the steps of identifying and isolating a highly purified starting material suitable for the preparation of a highly purified pharmaceutical grade final phthalazinedione product. The starting material is chemically treated to form a pharmaceutical grade final phthalazinedione product such that the final phthalazinedione product has a purity of at least 90% and wherein the process complies with GMP reproducibility standards.

In certain other embodiments of the process for reproducibly producing a highly purified pharmaceutical grade final phthalazinedione product, at least one additional step is included, wherein the starting material is chemically treated to form a highly purified intermediate product suitable for the preparation of the pharmaceutical grade final phthalazinedione product. The intermediate product is chemically treated to form the pharmaceutical grade final phthalazinedione product.

In yet further embodiments of the invention, the final phthalazinedione is 5-Amino-2,3-dihydro-1,4-phthalazinedione (luminol). In certain other embodiments, the final phthalazinedione is a sodium luminol, monosodium luminol, or any other analog or derivative, salt or ester thereof.

Certain aspects of the present invention provide methods of preparing the highly purified, pharmaceutical grade, final phthalazinedione product by chemically treating a highly purified intermediate. The batch of highly purified intermediate is prepared by combining several batches of the highly purified intermediate product into a batch process having the capacity for at 2000 lbs. For pharmaceutical use, the final phthalazinedione product is prepared under strict and reproducible conditions satisfying GMP standards. About 2000 lbs of the intermediate product is loaded into the batch process. In certain other embodiments, the intermediate is 3-Nitrophthalhydrazide.

In certain embodiments of the process for reproducibly producing a highly purified pharmaceutical grade final phthalazinedione product, the starting material is 90% pure as determined by HPLC. In certain embodiments the starting material is a highly purified form of 3-nitrophthalic acid. In certain embodiments, the intermediate material is a highly purified form of 3-nitrophthalhydrazide, having a purity of at least 90%.

In certain embodiments of the process for reproducibly producing a highly purified pharmaceutical grade final phthalazinedione product, the final phthalazinedione product meets GMP standards. In yet further embodiments, the production of the final phthalazinedione having a purity of at least 90%, or more preferably at least 95%, or more preferably at least 99% or most preferably at least 99.6% is reproducibly produced to meet GMP standards. The purity of the final phthalazinedione product also includes 91%, 92%, 93%, 94%, 96%, 97%, 98%, 99.1%, 99.2%, 99.3%, 99.4%, 99.5%, 99.6%, 99.7%, 99.8% and all specific values, ranges and sub-ranges therewithin.

To facilitate ease of use and improved bioavailability, it has been surprisingly found that the final phthalazinedione product can be produced such that it is capable of crossing the blood-brain barrier. In certain embodiments of the invention provide pharmaceutical compositions having the highly purified phthalazinedione products produced from the processes disclosed herein. In certain embodiments of the process for reproducibly producing a highly purified pharmaceutical grade final phthalazinedione product, the final phthalazinedione product is prepared such that it is capable of crossing the human blood-brain barrier. In certain embodiments the final phthalazinedione produced has a molecular weight of less than 500 grams-mol$^{-1}$. In certain other embodiments, the final phthalazinedione product has a molecular weight of 199.14 grams-mol$^{-1}$. In certain embodiments of the pharmaceutical compositions herein disclosed, the phthalazinedione product is formulated such that it is capable of crossing the human blood-brain barrier.

In yet further embodiments of the process for reproducibly producing a highly purified pharmaceutical grade final phthalazinedione product, the process includes identifying and isolating a highly purified form of 3-nitrophthalic acid having a purity of at least 99% as determined by HPLC analysis. The 3-nitrophthalic acid is chemically treated to produce 3-nitrophthalhydrazide having a purity of at least 99% as determined by HPLC analysis. The 3-nitrophthalhydrazide is chemically treated to produce monosodium luminol having a purity of at least 99.6% as determined by HPLC analysis and a product yield of at least 20 wt %.

In certain embodiments of the process for reproducibly producing a highly purified pharmaceutical grade final phthalazinedione product, the intermediate product is 3-nitrophthalahydrazide. In preparing the final phthalazinedione product from the highly purified 3-nitrophthalhydrazide, a solution of 3-Nitrophthalhydrazide and Sodium hydroxide in water is prepared. Water for injection (WFI) is charged to a reactor followed by sodium hydroxide pellets to form a clear solution. The highly purified intermediate product, such as 3-nitrophthalahydrazide, is charged to the clear solution to form a slurry that is dark brown in color. The sodium hydroxide and 3-nitrophthalhydrazide solution is then transferred to a hydrogenator. In certain aspects of the invention, the hydrogenator is a Biazzi hydrogenator. The solution is then hydrogenated with 5% Pd/C Johnson Matthey type 87L catalyst at 40° C. until hydrogen uptake is complete after the expected reaction time of 1 to 2 hours. An IPC is taken to confirm that the hydrogenation is complete. The catalyst is removed by filtration and the filtrate concentrated to approximately 25% of its original volume by distillation. In other embodiments of the invention, the solution is hydrogenated at 40° C./3 Bar with 1% Pd/C (Palladium on Charcoal) Johnson Matthey type 87L catalyst. The solution is cooled to 0-6° C. and held for crystallization to take place. Crystallization may require between 36-48 hours.

The hydrogenated solution is then filtered off and washed. An IPC is optionally taken to ensure that the pH of the product is within specification. If required the product is further washed until the pH is within the specification range.

While other methods are contemplated, the hydrogenated solution is filtered through a cartridge having a surface area of about 0.025 m2/kg surface area charged. The hydrogenated solution can also be filtered through a CUNO Zeta carbon cartridge. Sodium hydroxide is then added to the filtered solution. In certain specific embodiments, 32% sodium hydroxide is added to the filtered solution. The solution is then distilled. In some embodiments, the solution is distilled to 3.9-4.9 volumes and crystallized at 18° C.-24° C. Prior to crystallization, water is distilled out to reduce the volume down to 3.9 to 4.9 Liters (volumes) per kilo of sodium luminol. Ethanol is then added to the solution and stirred out for 1 to 2 hours until the crystallization is completed at about 7-13° C. The final phthalazinedione product is then isolated. In some other embodiments, the final phthalazinedione is isolated on an agitated filter-dryer and washed with ethanol. In certain embodiments, the final phthalazinedione product is recrystallized from solution containing 1 mol/L of sodium hydroxide solution (at 20 wt %). The final phthalazinedione product is then partially dried. The drying process from start to finish takes approximates 60-90 minutes. The product is then sieved and then dried under vacuum again until the water content is less than 1.0% and the ethanol content is less than 0.50% and the product has constant weight. The final product is sieved through a 1 mm mesh. The yield is up to 70%, up to 60%, up to 50%, up to 40%, up to 38%.

The components are for the manufacturing of the highly purified phthalazinedione are selected to produce a final phthalazinedione product that is highly purified. The intermediate product, preferably 3-Nitrophthalhydrazide, has a formula weight of 207.14, a purity of greater than or equal to 97% and has a yellow, powder composition. The sodium hydroxide has a formula weight of 40 and a titration purity of 98%, with a white pellet appearance. The WFI is a clear liquid with no detectable oxidizable substances and TOC of less than 500 ppb. The WFI has a conductivity of less than 1.1 µS/cm at 20° C. Methanol containing less than 0.0005% non-volatile matter and less than 0.05% water is used in this process. Gas chromatography of the methanol used herein demonstrates a purity of greater than 99.8%. Ethanol used in the process of the present invention has a purity of 99.7% as determined by gas chromatography with less than 0.05% impurities. The acidity and alkalinity are less than 0.01 ml N %. There were less than 0.01% higher alcohols in the ethanol solution and less than 0.3% water. 5% Palladium on Charcoal was used, having a water content of between 50.0 and 65%. Hydrogen having a purity of 99.995% was used.

The final phthalazinedione product produced from this process has a purity of at least 99%. All values and ranges therein are also contemplated. Potential impurities came from the intermediate product. For example, when the 3-nitrophthalhydrazide is reacted with a stoichiometric amounts of hydrogen during processing. Impurities are also due to the use of ethanol in the washing of the final product. This is the only organic solvent used in the process. Palladium on Charcoal may also be a contributory factor. The present invention contemplates all embodiments wherein these impurities are removed to further improve the purity of the final phthalazinedione product.

In certain embodiments of the present invention, the process of preparing the final pharmaceutical-grade phthalazinedione product does not include an intermediate. In certain other embodiments of the present invention, the preparation of the final phthalazinedione from the starting material includes several intermediates and intermediate steps.

In certain specific embodiments, the present invention provides a commercial process for producing the final phthalazinedione product. In some embodiments the process is optionally either a batch or a continuous batch process. For example, a batch of 1600 lbs of a highly purified form of 3-nitrophthalic acid is loaded into a reactor and the highly purified starting material is suspended in a solution of a weak acid and water. In some embodiments, a suspension is formed. In certain embodiments, the weak acid includes acetic acid. The suspension is then warmed and hydrated. In certain embodiments, the suspension is charged with hydrazine hydrate over 1 to 2 hours. In other embodiments, the suspension is optionally charged with additional hydrazine hydrate and warmed back to reflux and subsequently heated for a further 4 to 10 hours or more preferably 6 to 8 hours. In certain embodiments, the suspension is warmed to a temperature of about 50° C. to about 80° C. In further embodiments, the suspension is warmed to about 60° C. to about 75° C. In subsequent steps, the hydrated solution is then cooled to about 40° C. to about 70° C. or more preferably about 50° C. to about 60° C. and sampled for IPC. The solution is then further cooled to about 10° C. to about 30° C. or more preferably to about 14° C. to about 20° C. At least 200 lbs, and more preferably at least 400 lbs, of the isolated intermediate product is then isolated. In certain specific, though not exhaustive embodiments, the intermediate product is isolated by filtration. The isolated intermediate product is then washed and dried to constant weight. In some embodiments, the isolated intermediate product is washed twice with water (2 vol. each) and dried under vacuum at about 40° C. to about 70° C. or more preferably to about 50° C. to about 60° C. In some other embodiments, the intermediate is 3-Nitrophthalhydrazide. In preparing the final phthalazinedione product at least 2, and more preferably at least 3, batches of the 3-Nitrophthalhydrazide intermediate product are combined to form a batch of at least about 900 lbs, or more preferably at least about 1600 lbs. A solution of 3-Nitrophthalhydrazide and Sodium hydroxide in water is prepared. The sodium hydroxide and 3-nitrophthalhydrazide solution is then transferred to a hydrogenator. In certain embodiments of the invention, the hydrogenator is a Biazzi hydrogenator. In certain other embodiments, the sodium hydroxide and 3-nitrophthalyhydrazide solution is transferred to the hydrogenator via a mobile vessel. The solution is hydrogenated until hydrogen uptake is complete after the expected reaction time of 1 to 2 hours. In certain specific embodiments of the invention, the solution is hydrogenated at 40° C./3 Bar with 1% Pd/C Johnson Matthey type 87L catalyst. The hydrogenated solution is then filtered. In certain specific embodiments, the hydrogenated solution is filtered through a cartridge having a surface area of about 0.025 m2/kg surface area charged. In certain embodiments, the hydrogenated solution is filtered through a CUNO Zeta carbon cartridge. Sodium hydroxide is then added to the filtered solution. In certain specific embodiments, 32% sodium hydroxide is added to the filtered solution. The solution is then distilled. In certain specific embodiments, the solution is distilled to 3.9-4.9 volumes and crystallized at 18° C.-24° C. Ethanol is then added to the solution and stirred out for 1 to 2 hours until the crystallization is completed at about 7-13° C. The final phthalazinedione product is then isolated. In certain specific embodiments, the final phthalazinedione is isolated on an agitated filter-dryer and washed with ethanol. In certain embodiments, the final phthalazinedione product is recrystallized from a solution of containing 1 mol/L sodium hydroxide solution (at 20 wt %). The final phthalazinedione product is then partially dried. The product is then sieved and then dried again until the water content is less than 1.0% and the ethanol content is less than 0.50%. At least 300 lbs of a final pharmaceutical-grade, highly purified phthalazinedione is isolated.

Examples of the highly purified, pharmaceutical grade, phthalazinedione derivatives include, but are not limited to, 5-amino-2,3-dihydrophthalazine-1,4-dione (luminol), 6-amino-2,3-dihydrophthalazine-1,4-dione (isoluminol), 5-amino-2,3-dihydrophthalazine-1,4-dion-8-yl(luminyl), N-bromo-5-amino-2,3-dihydrophthalazine-1,4-dione, N-chloro-5-amino-2,3-dihydrophthalazine-1,4-dione, N-fluoro-5-amino-2,3-dihydrophthalazine-1,4-dione, N-iodo-5-amino-2,3-dihydrophthalazine-1,4-dione, N-methyl-5-amino-2,3-dihydrophthalazine-1,4-dione, N-ethyl-5-amino-2,3-dihydrophthalazine-1,4-dione, N-propyl-5-amino-2,3-dihydrophthalazine-1,4-dione, N-isopropyl-5-amino-2,3-dihydrophthalazine-1,4-dione, N-methanoyl-5-amino-2,3-dihydropthalazine-1,4-dione, N-ethanoyl-5-amino-2,3-dihydrophthalazine-1,4-dione, N-propanoyl-5-amino-2,3-dihydrophthalazine-1,4-dione, N-hydroxyl-5-amino-2,3-dihydrophthalazine-1,4-dione, N-carboxyl-5-amino-2,3-dihydrophthalazine-1,4-dione, N-methanol-5-amino-2,3-dihydrophthalazine-1,4-dione, N-ethanol-5-amino-2,3-dihydrophthalazine-1,4-dione, N-propanol-5-amino-2,3-dihydrophthalazine-1,4-dione, N-methenyl-5-amino-2,3-dihydrophthalazine-1,4-dione, N-ethenyl-5-amino-2,3-dihydrophthalazine-1,4-dione, N-propenyl-5-amino-2,3-dihydrophthalazine-1,4-dione, N-methoxy-5-amino-2,3-dihydrophthalazine-1,4-dione, N-ethoxy-5-amino-2,3-dihydrophthalazine-1,4-dione, N-propoxy-5-amino-2,3-dihydrophthalazine-1,4-dione, N,N-dimethyl-5- amino-2,3-dihydrophthalazine-1,4-dione, N-acetylcysteine-5-amino-2,3-dihydrophthalazine-1,4-dione, and N-acetylglutathione-5-amino-2,3-dihydrophthalazine-1,4-dione. Enantiomers, isomers, tautomers, esters, amides, salts, solvates, hydrates, analogues, metabolites, free bases, or prodrugs of the phthalazinedione or its derivative are also contemplated by the invention.

Highly Purified Phthalazinediones and Compositions Thereof:

In certain embodiments, the invention includes a pharmaceutical composition comprising a highly purified phthalazinedione, prepared as described above. In certain embodiments, the phthalazinedione is luminol, sodium luminol, monosodium luminol, or any other analog, salt or ester thereof. In certain other embodiments, the composition further comprises an amino acid, antibiotic, antiviral agent, anti-inflammatory agent, antioxidant, immunomodulator, a reductant, an oxidative protector, a steroid, a vitamin or any combination thereof.

The phthalazinedione compounds of the present invention are preferably incorporated into pharmaceutical forms suitable for administration by oral, nasal, mucosal, vaginal, rectal, transdermal, or parenteral routes, including subcutaneous, intramuscular, intravenous, and intraperitoneal, topical or ocular e.g., tablet, capsule, granule, powder, solution, suspension, microsphere, liposome, colloid, lyophilized composition, gel, lotion, ointment, cream, spray, and suppository, and preferably include pharmaceutically acceptable excipients, carriers, adjuvants, diluents, or stabilizers as is well known to the skilled in the art.

The phthalazinedione may be a derivative compound containing a substituent that enhances the activity, stability, transmucosal activity, or other property of the compound. Such a derivative compound may be an amino phthalazinedione or a phthalazinedione comprising a haloamino, alkylamino, acylamino, alkanolamino, alkenylamino, alkoxyamino, haloalkylamino, allylamino, or sulfhydrylamino (thiolamino or mercaptoamino) group or other substituents that confer a preferred function on the compound. Furthermore, the phthalazinedione may be a bromoamino, chloroamino, fluoroamino, iodoamino, methylamino, ethylamino, propylamino, isopropylamino, methanoylamino (formylamino), ethanoylamino(acetylamino), propanoylamino, hydroxylamino, carboxylamino, methanolamino, ethanolamino, propanolamino, methenylamino, ethenylamino, propenylamino, methoxyamino, ethoxyamino, propoxyamino, or dimethylamino derivative.

Examples of such phthalazinedione derivatives include, but are not limited to, 5-amino-2,3-dihydrophthalazine-1,4-dione (luminol), 6-amino-2,3-dihydrophthalazine-1,4-dione (isoluminol), 5-amino-2,3-dihydrophthalazine-1,4-dion-8-yl (luminyl), N-bromo-5-amino-2,3-dihydrophthalazine-1,4-dione, N-chloro-5-amino-2,3-dihydrophthalazine-1,4-dione, N-fluoro-5-amino-2,3-dihydrophthalazine-1,4-dione, N-iodo-5-amino-2,3-dihydrophthalazine-1,4-dione, N-methyl-5-amino-2,3-dihydrophthalazine-1,4-dione, N-ethyl-5-amino-2,3-dihydrophthalazine-1,4-dione, N-propyl-5-amino-2,3-dihydrophthalazine-1,4-dione, N-isopropyl-5-amino-2,3-dihydrophthalazine-1,4-dione, N-methanoyl-5-amino-2,3-dihydrophthalazine-1,4-dione, N-ethanoyl-5-amino-2,3-dihydrophthalazine-1,4-dione, N-propanoyl-5-amino-2,3-dihydrophthalazine-1,4-dione, N-hydroxyl-5-amino-2,3-dihydrophthalazine-1,4-dione, N-carboxyl-5-amino-2,3-dihydrophthalazine-1,4-dione, N-methanol-5-amino-2,3-dihydrophthalazine-1,4-dione, N-ethanol-5-amino-2,3-dihydrophthalazine-1,4-dione, N-propanol-5-amino-2,3-dihydrophthalazine-1,4-dione, N-methenyl-5-amino-2,3-dihydrophthalazine-1,4-dione, N-ethenyl-5-amino-2,3-dihydrophthalazine-1,4-dione, N-propenyl-5-amino-2,3-dihydrophthalazine-1,4-dione, N-methoxy-5-amino-2,3-dihydrophthalazine-1,4-dione, N-ethoxy-5-amino-2,3-dihydrophthalazine-1,4-dione, N-propoxy-5-amino-2,3-dihydrophthalazine-1,4-dione, N,N-dimethyl-5-amino-2,3-dihydrophthalazine-1,4-dione, N-acetylcysteine-5-amino-2,3-dihydrophthalazine-1,4-dione, and N-acetylglutathione-5-amino-2,3-dihydrophthalazine-1,4-dione. Enantiomers, isomers, tautomers, esters, amides, salts, solvates, hydrates, analogues, metabolites, free bases, or prodrugs of the phthalazinedione or its derivative are also contemplated by the invention.

In an embodiment of the invention, phthalazinediones can be used to either facilitate or inhibit electron flow in mitochondria, and thus control ATP production. For example, in vitro, at the low dose of 20-50 µM, amino phthalazinediones facilitate electron flow at mitochondrial Complex III, thereby increasing ATP production, DNA synthesis, and cell cycling, for cell growth. At an intermediate dose of 100 µM, amino phthalazinediones slow down electron flow, with concomitant effects on ATP production, DNA synthesis, and cell cycling, so that differentiation can proceed. At the high dose of 200 µM, amino phthalazinediones completely stop ATP production, DNA synthesis, and cell cycling in the stressed cell, such that the cell becomes quiescent but does not die.

Thus, phthalazinediones of the invention may be used to control cell fates and serve as redox buffers for the redox- and thiol-sensitive energy producing pathways in the mitochondrion, signaling pathways at the cell plasma membrane, and glutamate uptake and cytokine secretion by astrocytes in the central nervous system (Trotti et al., J. Biol. Chem. 271: 5976-5979, 1996). In particular, amino phthalazinediones catalyze disulfide cross-linkages in the adenine nucleotide translocase (ANT) of the mitochondrial anion channels and in the megapores, which prevents energy production, increases production of the potent signal transducers hydrogen peroxide (H2O2) and superoxide (O2-) (Zamzami et al., Oncogene 16: 1055-1063, 1998; Constantini et al., J. Biol. Chem. 271: 6746-6751, 1996), and liberates the apoptosis-inducing factors cytochrome c and AIF.

In one embodiment of the invention, therapy includes combined treatment with phthalazinediones and compounds to replace the lost thiols, oxidatively protect the phthalazinedione, eliminate the source of stress, or otherwise support the subject in fighting a particular condition. A compound that is an amino acid, antibiotic, antiviral agent, anti-inflammatory agent, antioxidant, immunomodulator, reductant, oxidative protector, steroid, or vitamin may be beneficial. Compounds such as a cysteine (e.g., acetyl cysteine, N-acetylcysteineamide), glutathione, lipoic acid (e.g., alpha lipoic acid, dehydrolipoic acid), hydralazine, thioredoxin, biopterin (e.g., tetrahydropterin, sepiapterin), glucocorticoid, dexamethasone, rasagiline, ferulic acid, minocyline, menadione, tetracycline, isosorbate dinitrate, dextromethorphan, or mixtures thereof may be used. The additional compound may be administered simultaneously, separately, or sequentially.

The preferred active ingredients may be formulated into a pharmaceutical composition with one or more pharmaceutically acceptable excipients. For example, a pharmaceutical composition may comprise a phthalazinedione, a glutathione, and one or more pharmaceutically acceptable excipients. The pharmaceutical composition may be in the form of a tablet, capsule, granule, powder, solution, suspension, microsphere, liposome, colloid, lyophilized composition, gel, lotion, ointment, cream, spray, or suppository and administered intravenously, intramuscularly, intraperitoneally, subcutaneously, orally, nasally, mucosally, transdermally, parenterally, vaginally, or rectally. A therapeutically effective amount of the phthalazinedione or a pharmaceutical composition comprising a therapeutically effective amount of the phthalazinedione is administered to a subject in metabolic distress, to maintain the desired redox status and mitochondrial energy production, as well as the redox-sensitive MAP kinase-Ras PT3K signal transduction pathways.

EXEMPLIFICATION

The invention will be further understood by the following example. However, those skilled in the art will readily appreciate that the specific experimental details are only illustrative and are not meant to limit the invention as described herein, which is defined by the claims which follow thereafter. The contents of any patents, patent applications, patent application publications and references cited throughout this specification are hereby incorporated by reference in their entireties.

Example—Preparation of a Highly Purified Monosodium Luminol Purity Analysis of the Starting Material 3-Nitrophthalic Acid HPLC analysis is used to analyze a batch of 3-nitrophthalic acid to confirm a purity of at least 90%. A small sample of the 3-nitrophthalic acid solution is placed into a 100 ml volumetric flask and dissolved in a dissolution solvent. Empower software uses vectors to characterize spectra. The software generates from a spectrum a vector in a N-dimensional vector space, where N is the number of wavelengths in the spectrum. The vector has two properties: length and direction. Spectra with the same shape have vectors that point in the same direction, which means the same N-dimensional angle. Spectra with different shapes have vectors that point in different directions. The angle between the two vectors is spectral contrast angle (SCA) and quantifies the magnitude of the shape difference between the spectra. The graphical representation of SCA variation versus time is the purity trace. Empower software calculates in the same way the non-ideal effects, giving the threshold angle that is graphically represented versus time by the threshold trace. The small solution of 3-nitrophthalic acid is characterized by HPLC to determine it's purity. A purity of 90% is detected which satisfies the requirement for producing a highly purified final phthalazinedione product.

Preparing the Highly Purified Intermediate 3-Nitrophthalhydrazide

A 1600 lbs batch of the previously determined 90% pure 3-nitrophthalic acid starting material is loaded into a reactor. The highly purified starting material is suspended in a solution of acetic acid (1.48 vol) and water (3.28 vol) to form a suspension. The suspension is then warmed to between 60° C. and 75° C. and charged with hydrazine hydrate (1.2 mol eq) for 1 hour while maintaining the temperature between 60° C. and 75° C. The solution is heated to reflux for 16 hours then cooled to between 50° C. and 60° C. The solution is then sampled for IPC then further cooled to between 14° C. and 20° C. The approximately 300 lbs of intermediate 3-nitrophthalhydrazide product is isolated by filtration, then washed twice (2 vol each). The isolated intermediate is then dried under vacuum at 50° C. to 60° C. until a constant weight is achieved.

The steps recited above for the purity analysis of starting 3-nitrophthalic acid is repeated here for the isolated intermediate 3-nitrophthalhydrazide product to confirm it's purity of at least 90%.

Preparing the Highly Purified Final Sodium Luminol Product

A 900 lbs batch of the isolated intermediate 3-nitrophthalhydrazide product is prepared by combining three separate 300 lbs batch of the 90% 3-nitrophthalhydrazide product obtained from the previous steps.

A solution of the 900 lb bath of 90% pure 3-nitrophthalhydrazide product, sodium hydroxide (1.1 eq) and water for injection (8 vol) is formed and then transferred to a Biazzi hydrogenator via a mobile vessel. The solution is hydrogenated (13.2 vol including washes) at 40° C./3 Bar with 1% Pd/C (5%) Johnson Matthey type 87L catalyst until hydrogen uptake is complete after the expected reaction time of 1 to 2 hours. An IPC is taken to confirm hydrogenation is complete. The solution is filtered through CUNO Zeta carbon cartridges (surface area 0.02545 m2/kg of 3-nitrophthalhydrazide charged) then 32% sodium hydroxide solution is added (0.31 vol). The solution is distilled to 3.9 to 4.9 volumes and crystallized at 18° C. to 24° C. Ethanol (1 wt) is added and, after 1 hour stir-out, the crystallization is completed at between 7° C. and 13° C. The product is isolated on an agitated filter-dryer and washed with ethanol. The product is partially dried and tested against the color and purity specifications. After passing the color test, it is then sieved and dried again until the water content is less than 1.0% and the ethanol content is less than 0.5%.

HPLC analysis, as described above, is performed on the final sodium luminol product to confirm a purity of at least 90%.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A process for preparing 5-amino-2,3-dihydrophthalazine-1,4-dione monosodium salt, the process comprising the steps of:
   (i) providing a mixture of 3-nitrophthalic acid and acetic acid;
   (ii) reacting the mixture of 3-nitrophthalic acid and acetic acid with hydrazine hydrate to provide 3-nitrophthalhydrazide;
   (iii) providing a solution of 3-nitrophthalhydrazide and sodium hydroxide in water; and
   (iv) hydrogenating the solution of 3-nitrophthalhydrazide and sodium hydroxide in water to provide 5-amino-2,3-dihydrophthalazine-1,4-dione monosodium salt.

2. The process of claim 1, wherein the mixture of 3-nitrophthalic acid and acetic acid provided in step (i) is warmed to a temperature between 60° C. and 75° C. prior to step (ii).

3. The process of claim 1, wherein the ratio of the volume of acetic acid to the volume of water is 1.48:3.28.

4. The process of claim 1, wherein step (ii) is performed at a temperature between 60° C. and 75° C.

5. The process of claim 1, wherein the hydrazine hydrate is added over a period of one hour.

6. The process of claim 1, wherein the molar ratio of 3-nitrophthalic acid to hydrazine hydrate is 1.0:1.2.

7. The process of claim 1, wherein the 3-nitrophthalhydrazide provided in step (ii) is dried under vacuum at a temperature between 50° C. and 60° C. prior to step (iii).

8. The process of claim 1, wherein step (iv) is performed at a temperature of 40° C.

9. The process of claim 1, wherein step (iv) is performed at a pressure of 3 Bar.

10. The process of claim 1, wherein step (iv) is performed at a temperature of 40° C. and at a pressure of 3 Bar.

11. The process of claim 1, wherein step (iv) is performed over a period of one to two hours.

12. The process of claim 1, wherein the 5-amino-2,3-dihydrophthalazine-1,4-dione monosodium salt in step (iv) is provided via a crystallization from ethanol.

13. The process of claim 12, wherein the crystallization is performed at a temperature between 7° C. and 24° C.

14. The process of claim 13, wherein the crystallization is performed at a temperature between 7° C. and 13° C.

15. The process of claim 12, wherein the crystallization is performed over a period of one hour.

* * * * *